United States Patent [19]

Berges

[11] 4,174,323

[45] Nov. 13, 1979

[54] 1-(2-SULFAMIDOETHYL)-1,4-DIHYDRO-5H-TETRAZOLE-5-THIONE

[75] Inventor: David A. Berges, Wayne, Pa.

[73] Assignee: SmithKline Corporation, Philadelphia, Pa.

[21] Appl. No.: 921,681

[22] Filed: Jul. 3, 1978

Related U.S. Application Data

[62] Division of Ser. No. 805,197, Jun. 9, 1977, Pat. No. 4,117,123.

[51] Int. Cl.$^2$ .............................................. C07D 257/04
[52] U.S. Cl. ..................................................... 548/251
[58] Field of Search ...................... 260/308 D; 544/26

[56] References Cited

U.S. PATENT DOCUMENTS

| | | | |
|---|---|---|---|
| 3,578,674 | 5/1971 | Buckler et al. | 260/308 D |
| 3,743,646 | 7/1973 | Buckler et al. | 260/308 D |
| 3,840,535 | 10/1974 | Kaplan et al. | 544/26 |

*Primary Examiner*—Donald G. Daus
*Assistant Examiner*—D. B. Springer
*Attorney, Agent, or Firm*—Joseph A. Marlino; Richard D. Foggio; William H. Edgerton

[57] ABSTRACT

Novel cephalosporins having various acyl substituents at the 7-position and a sulfamidoethyl substituted tetrazolylthiomethyl group at the 3-position of the cephem nucleus are prepared. These compounds have antibacterial activity.

3 Claims, No Drawings

1-(2-SULFAMIDOETHYL)-1,4-DIHYDRO-5H-TETRAZOLE-5-THIONE

This is a division of application Ser. No. 805,197 filed June 9, 1977, now U.S. Pat. No. 4,117,123, issued 9/26/78.

This invention relates to a new series of cephalosporin compounds having antibacterial activity and to intermediates useful for preparing them. The structures of the new compounds are characterized by having at the 3-position a sulfamidoethyl substituted tetrazole group.

Exemplary of the compounds of this invention are those represented by the following structural formula:

FORMULA I

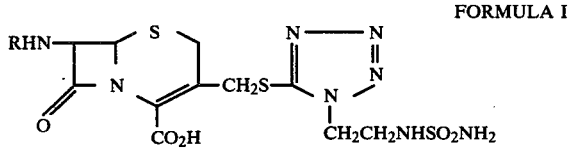

in which R represents a pharmaceutically acceptable acyl group known to be of utility as a substituent on the 7-amino group in the structures of known or prior art cephalosporins or on the 6-amino group in the structures of known or prior art penicillins.

Representative acyl substituents are:

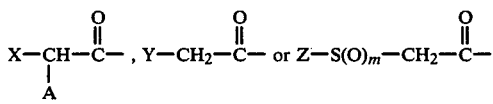

wherein:

X is thienyl, furyl, phenyl or phenyl monosubstituted with hydroxy, hydroxymethyl, formamido or ureido;

A is $NH_2$, OH, COOH, $SO_3H$, formyloxy or, when the α-C-hydrogen is absent, methoxyimino;

Y is cyano, sydnone, pyridone, thienyl, o-aminomethylphenyl, phenyl or tetrazolyl;

Z is methyl, trifluoromethyl, trifluoroethyl, pyridyl or cyanomethyl; and m is zero to two.

Each of the three partial structures above represent subgeneric groups of compounds covered by this invention.

Representative 7-acylamino substituents of the compounds of Formula I are listed below:
α-hydroxyphenylacetamido
α-aminophenylacetamido
α-amino-4-hydroxyphenylacetamido
trifluoromethylthioacetamido
2,2,2-trifluoroethylsulfinylacetamido
2,2,2-trifluoroethylthioacetamido
cyanoacetamido
α-carboxythienylacetamido
α-carboxyphenylacetamido
α-sulfophenylacetamido
methylsulfonylacetamido
cyanomethylthioacetamido
3-sydnoneacetamido
1-tetrazolylacetamido
2-thienylacetamido
α(Z)-(methoxyimino)-2-furanacetamido
4-pyridylthioacetamido
o-aminomethylphenylacetamido Others together with N-acylation procedures may be found in *Cephalosporins and Penicillins*, Flynn, Academic Press, 1972; U.S. Pat. Nos. 2,721,196 and 3,953,424; Belgian Pat. No. 832,725; German Pat. Nos. 2,127,285 and 2,406,165.

It will be recognized that the 4-carboxylic acid group of the compounds of Formula I may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such ester derivatives are included within the scope of this invention.

Also covered in this invention are the pharmaceutically acceptable, nontoxic derivatives of the compounds of Formula I from which they derive utility: the salts, as stated above easily split ester or ether derivatives of either a carboxy or hydroxy function, amide derivatives at an amino group contained in a 7-phenylglycylamino group, for example, the furyl-, pyranyl-, oxolanyl- or oxiranyl-carbonyl amides (i.e. Belgian Pat. No. 835,295), the solvates such as hydrates, glycolates or alcoholates. As examples of these, one skilled in the art would be able to prepare and use the alkali metal salts such as the sodium or potassium salts (for example using sodium or potassium 2-ethyl hexanoate), ammonium salts, organic amine salts such as those with procaine or dibenzylethylenediamine.

Other known cephalosporin modifications can be made by known synthetic procedures such as introduction of an α-methoxy group at position 7, preferably at the stage of the 7-aminocephalosporanic acid reactants disclosed below (IV), prior to N-acylation. Optical isomers are also possible such as with the mandeloyl or phenylglycyl substituents at 7. The D-forms of these subgeneric groups are preferred.

The compounds of this invention are most conveniently prepared by a displacement of the acetoxy group of a known 7-acylaminocephalosporanic acid (II) by 1-(2-sulfamidoethyl)-1,4-dihydro-5H-tetrazole-5-thione (III). Alternatively a similar displacement with the thione can be run on 7-aminocephalosporanic acid to give 7-amino-3-[1-(2-sulfamidoethyl)tetrazol-5-ylthiomethyl]-3-cephem-4-carboxylic acid (IV) which may then be N-acylated as known to the art as described above. Suitable protective groups may be used in either method as is known to the art (see "Protective Groups in Organic Chemistry", J.F.W. McOmie, Plenum Press, 1973, Chapters 2 and 3 for use of amino, carboxy, sulfo or hydroxyl protective groups).

For example, the t-butyl (for COOH) or t-butoxycarbonyl (for $NH_2$) groups are easily removed by treatment with trifluoroacetic acid.

The 1-aminoacid substituted tetrazole-5-thiones expressed in their tautomeric forms by Formula III are new compounds and are part of this invention.

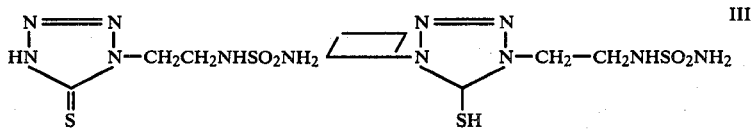

The invention also includes the alkali metal and ammonium salts of the compound of Formula III.

The compounds of Formula I have antibacterial activity against both Gram positive and Gram negative bacteria with minimum inhibitory concentrations (MIC's) in vitro from 0.4 to 200 μg/ml. Test results for 7-D-(- )-mandelamido-3-[1-(2-sulfamidoethyl)tetrazol-5-ylthiomethyl]-3-cephem-4-carboxylic acid, sodium salt, dihydrate (A) and 7-[α(Z)-(methoxyimino)-2-furanacetamido]-3-[1-(2-sulfamidoethyl)tetrazoyl-5-ylthiomethyl]-3-cephem-4-carboxylic acid sodium salt (B) are:

|  | A | B | Cefazolin |
| --- | --- | --- | --- |
| S. aureus HH 127 | 1.6 | 0.8 | 0.4 |
| S. aureus SK 23390 | 0.2 | 0.8 | 0.2 |
| S. aureus villaluz SK 70390 | 12.5 | 200 | 50 |
| Strep. faecalis HH 34358 | 12.5 | 25 | 3.1 |
| E. coli SK 12140 | 0.4 | 1.6 | 0.8 |
| E. coli HH 33779 | 0.4 | 1.6 | 1.6 |
| Kleb. pneumo. SK 4200 | 0.4 | 0.4 | 1.6o |
| Kleb. pneumo. SK 1200 | 0.2 | 1.6 | 0.8 |
| Salmonella ATCC 12176 | 0.1 | 0.4 | 0.4 |
| Pseudo. aeru. HH 63 | >200 | 200 | >200 |
| Serratia marc. ATCC 13880 | 0.8 | 3.1 | 25 |
| Proteus morgani 179 | 0.8 | 1.6 | 50 |
| Entero. aerog. ATCC 13048 | 0.8 | 3.1 | 1.6 |
| Entero. cloacae HH 31254 | 0.4 | 1.6 | 0.8 |
| Proteus mirabilis HH 44 | 0.4 | 0.8 | 3.1 |

Compound A gave an $ED_{50}$ in mice of 0.26 against E. coli as well as 0.195 mg/kg against Kleb. pneumo. (s.c.).

Pharmaceutical compositions having antibacterial activity which comprise a pharmaceutical carrier containing an active but nontoxic quantity of a compound of Formula I as well as methods of combatting bacterial infections by administering such a composition to an infected animal or human host in a nontoxic amount sufficient to combat such infections are also objects of this invention. The administration may be orally or by parenteral injection such as subcutaneously, intramuscularly or intravenously. The injection of suitably prepared sterile solutions or suspensions containing an effective, nontoxic amount of the new cephalosporin compound is the preferred route of administration.

The compounds of Formula I are formulated and administered in the same manner as other prior art cephalosporins such as cephazolin or cephalothin. The dosage regimen comprises administration, preferably by injection, of an active but nontoxic quantity of a compound of Formula I selected from the dosage unit range of from about 250 mg. to 600 mg. with the total daily dosage regimen being from about 750 mg. to 6 g. The precise dosages are dependent upon the age and weight of the subject and on the susceptibility of the infection being treated to each individual. These can be determined by those skilled in the art based on the data disclosed herein compared with that available to the art attained with the known cephalosporins outlined hereinbefore.

The following examples illustrate the invention but are not to be construed as limiting the scope thereof.

Temperatures are in degrees Centigrade (°C.) unless otherwise stated.

EXAMPLE 1

To a solution of 20.4 g. (0.20 mol) of N-(2-aminoethyl)acetamide in 200 ml. of 95% ethanol was added 27.9 ml. (0.20 mol) of triethylamine and 12.0 ml. (0.20 mol) of carbon disulfide. The exothermic reaction reached reflux and then cooled to ambient temperature over a 1.5 hour period. Methyl iodide (28.4 g; 0.20 ml.) was added which again produced an exothermic reaction. After 1.75 hours the reaction mixture was evaporated to dryness and the solid residue was dissolved in 200 ml. of water. The aqueous solution was extracted twice with 250 ml. portions of ethyl acetate. The extracts were combined, shaken with sodium thiosulfate, dried ($MgSO_4$) and evaporated to dryness to give methyl 2-acetamidoethyldithiocarbamate.

To a solution of 38.4 g. (0.198 mol) of methyl 2-acetamidoethyldithiocarbamate in 100 ml. of 95% ethanol was added a solution of 13.5 g. (0.208 mol) of sodium azide in 100 ml. of water. The reaction mixture was refluxed for 24 hours then cooled and concentrated under reduced pressure to about half volume. The solution was cooled to 15° and 50 ml. of 6 N sulfuric acid was added. The acidic solution was filtered and the filtrate was concentrated to about 100 ml. and chilled at 5° C. to induce crystallization of 1-(2-acetamidoethyl)-tetrazole-5-thiol which was collected by filtration, mp 139°-139.5° C. Additional amounts of the product were obtained by continuous extraction of the filtrate with ethyl acetate.

A solution of 9.3 g. (0.050 mol) of 2,4-dinitrofluorobenzene in 50 ml. of acetone was added to a solution of 9.35 g. (0.050 mol) of 1-(2-acetamidoethyl)tetrazole-5-thiol and 6.85 ml. (0.050 mol) of triethylamine in 100 ml. of acetone and the reaction mixture was stirred for 1 hour. The solid material was collected by filtration and recrystallized from acetonitrile to give 1-(2-acetamidoethyl)-5-(2,4-dinitrophenylthio)tetrazole, mp 197°-198° C.

A mixture of 6.5 g. (0.02 mol) of 1-(2-acetamidoethyl)-5-(2,4-dinitrophenylthio)tetrazole, 100 ml. of 12 N hydrochloric acid and 100 ml. of 95% ethanol was refluxed for 4.5 hours. The mixture was evaporated to dryness to give a gummy residue which crystallized upon addition of ethanol to give 1-(2-aminoethyl)-5-(2,4-dinitrophenylthio)tetrazole hydrochloride, mp 217°-219° C. (d).

Triethylamine (1.0 g., 0.01 mol) was added to a suspension of 1.73 g. (0.005 mol) of the above tetrazole hydrochloride in 50 ml. of dry tetrahydrofuran. The suspension was cooled to 0° C. At that temperature 0.885 g. (0.005 mol) of N-tert-butylsulfamoyl chloride in 40 ml. of dry tetrahydrofuran was added. After 30 minutes of stirring, the triethylamine hydrochloride was separated by filtration. The filtrate was evaporated to dryness. The residue was suspended in water, a little dilute hydrochloric acid was added and the suspension was extracted with ethyl acetate. The extract was drived over MgSO₄ and stripped in vacuo to give the desired 1-(2-N-tert-butylsulfamidoethyl)-5-(2,4-dinitrophenylthio)tetrazole as a yellow solid. This reaction was repeated using 51.9 g. of the tetrazole hydrochloride.

The tert-butyl compound (51.5 g.) was added to 500 ml. of trifluoroacetic acid and 250 ml. of m-dimethoxybenzene. The mixture was stirred at room temperature for 3 hours then stripped of the trifluoroacetic acid in vacuo. The dimethoxybenzene solution was diluted with 1.5 l. of ether to give a yellow precipitate. The solid was chromatographed on silica using 50:50 acetone/chloroform as eluant. The product-containing eluate was stripped. The residue was triturated with 100 ml. of ethanol to give a product which after recrystallization from ethanol gave 1-(2-sulfamidoethyl)-5-(2,4-dinitrophenylthio)tetrazole, mp 123°–125° C. as the hemihydrate.

The sulfamido intermediate (25.55 g., 0.065 mol) was suspended in 300 ml. of dry methanol and treated with 17 ml. of 25% sodium methoxide in methanol at room temperature with stirring. The methanol was stripped off in vacuo and the residue dissolved in 300 ml. of water. After filtering, the aqueous solution (pH 9.0) was extracted with ethyl acetate and then adjusted to pH 7.5 with dilute hydrochloric acid and again extracted with ethyl acetate.

The aqueous layer was taken to pH 1.5 with dilute hydrochloric acid and extracted with ethyl acetate. This extract was dried (MgSO₄) and stripped in vacuo to give a yellow powder, 1-(2-sulfamidoethyl)-1,4-dihydro-5H-tetrazole-5-thione.

A mixture of 4.49 g. of 7-(D-(-)-mandelamido)-cephalosporanic acid, sodium salt hydrate in 10 ml. of water with 1.92 g. of 1-(2-sulfamidoethyl)-1,4-dihydro-5H-tetrazole-5-thione and 0.84 g. of sodium bicarbonate in 10 ml. of water was heated at 65° for four hours while keeping the pH at 7.4–7.6. The cooled reaction mixture was extracted with ethyl acetate. The aqueous layer was applied to an XAD-4 column (a nonionic resin which is a crosslinked copolymer of styrene-divinylbenzene) and eluted first with water and then 50% aqueous methanol. The methanol was stripped in vacuo from the pooled product-containing fractions. The remaining aqueous solution was treated with dilute hydrochloric acid to a pH of 1.5 and then extracted with ethyl acetate. After drying (MgSO₄) the extracts, the ethyl acetate was removed in vacuo to give a residue which was dissolved in dry methanol and adjusted to pH of 7.0 with 12.5% sodium methoxide in methanol. Diluting with ether gave a white solid. This material was dissolved in water and eluted with water through a Bio-Gel P-2 column (a copolymerized acrylamide-N,N-methylene-bisacrylamide porous beads available from Bio-Rad). The product-containing eluate was lyophilized to give 7-[D-(-)-mandelamido]-3-[1-(2-sulfamidoethyl)tetrazole-5-ylthiomethyl]-3-cephem-4-carboxylic acid, sodium salt hemihydrate. Anal. calcd. for $C_{19}H_{21}NaN_6H_7S_3 \cdot \frac{1}{2} H_2O$: C, 37.93; H, 3.69; N, 18.63. Found: C, 37.63; H, 3.85; N, 18.66.

EXAMPLE 2

A mixture of 2.15 g. (0.0096 mol) of 7-[α(Z)-(methoxyimino)-2-furanacetamido]cephalosporanic acid sodium salt in a solution of 0.78 (0.0096 mol) of sodium bicarbonate in 100 ml. of water with 4.05 g. (0.0091 mol) of 1-(2-sulfamidoethyl)-1,4-dihydro-5H-tetrazole-5-thione was heated at 65° C. for 6 hours during which time the pH was maintained at a pH of 7.6–7.8 with dilute sodium bicarbonate. After cooling, the reaction mixture (pH 7.0) was extracted with ethyl acetate. The aqueous layers were taken to pH of 1.5 with dilute hydrochloric acid and reextracted with ethyl acetate. After drying, the latter extract was stripped off in vacuo to give a yellow solid which was purified with XAD-4 and Bio-Gel P columns as described in Example 1 to give a lyophilized product, 7-[α(Z)-(methoxyimino)-2-furanacetamido]-3-[1-(2-sulfamidoethyl)tetrazole-5-ylthiomethyl]-3-cephem-4-carboxylic acid hydrate. Anal. calcd. for $C_{18}H_{20}N_2NaO_8S_3 \cdot 1 H_2O$: C, 34.45; H, 3.53; N, 20.09. Found: C, 35.47; H, 3.31; N. 20.68.

EXAMPLE 3

A mixture of 5.22 g. (10.0 mmol) of 7-(D-α-t-butoxycarbonylamino-4-hydroxyphenylacetamido)cephalosporanic acid and an excess (15.0 mmol) of 1-(2-sulfamidoethyl)-1,4-dihydro-5H-tetrazole-5-thione in 75 ml. of pH 6.4 phosphate buffer solution is treated with sufficient sodium bicarbonate to give a pH of 6.4. The mixture is heated at 70° for 3 hours, cooled, acidified with dilute hydrochloric acid to pH 2 and extracted with ethyl acetate. Removal of the ethyl acetate in vacuo gives the t-boc derivative of the desired compound. This derivative is stirred at 25° C. with 25 ml. of trifluoroacetic acid and 25 ml. of 1,3-dimethoxybenzene for 2 hours. The mixture is evaporated to dryness in vacuo, ethyl acetate is added to the residue and the precipitated salt is collected. This is dissolved in water and treated with Amberlite IR-45 weakly basic ion-exchange resin. The solution is lyophilized to give 7-(D-α-amino-4-hydroxyphenylacetamido)-3-[1-(2-sulfamidoethyl)tetrazole-5-ylthiomethyl]-3-cephem-4-carboxylic acid. Similar treatment of the t-boc derivatives of the 7-DL-(α-aminophenylacetamido)cephalosporanic acid gives the corresponding 7-DL-(α-aminophenylacetamido)-3-[1-(2-sulfamidoethyl)tetrazole-5-ylthiomethyl]-3-cephem-4-carboxylic acid.

EXAMPLE 4

A mixture of an excess (12.2 mmol) of 1-(2-sulfamidoethyl)-1,4-dihydro-5H-tetrazole-5-thione, 20.3 mmol of sodium bicarbonate and 8.1 mmol of 7-trifluoromethylthioacetamidocephalosporanic acid in 50 ml. of water is stirred at 70° for 5 hours. The reaction mixture is cooled and applied to an XAD-2 column and eluted with water and then methanol. The product-containing effluent is evaporated to dryness to give a residue which is dissolved in a small amount of water and lyophilized to give 7-trifluoromethylthioacetamido-3-[1-(2-sulfamidoethyl)tetrazole-5-ylthiomethyl]-3-cephem-4-carboxylic acid sodium salt. Substituting 7-(2-thienylacetamido)-cephalosporanic acid gives 7-(2-thienylacetamido)-3-[1-(2-sulfamidoethyl)tetrazole-5-ylthiomethyl]-3-cephem-4-carboxylic acid sodium salt.

Stoichiometric quantities of cephalosporanic acids having the individual 7-acylamino substituent listed hereabove may be substituted in Examples 1–3 with variations which will be obvious to those skilled in this art.

EXAMPLE 5

An injectable pharmaceutical composition is formed by adding sterile saline solution (2 ml.) to 500 mg. of the product of Example 1. This material is injected parenterally four times daily to a human patient infected with susceptible bacteria. Other compounds of this invention may be similarly used.

What is claimed is:

1. 1-(2-Sulfamidoethyl)-1,4-dihydro-5H-tetrazole-5-thione and its alkal metal and ammonium salts.
2. The compound of claim 1 being 1-(2-sulfamidoethyl)-1,4-dihydro-5H-tetrazole-5-thione.
3. The compound of claim 1 being the sodium salt.

* * * * *